United States Patent [19]

Klieman et al.

[11] Patent Number: 4,522,207
[45] Date of Patent: Jun. 11, 1985

[54] SPRING ACTIVATED HEMOSTATIC CLIP APPLICATOR

[75] Inventors: Charles H. Klieman, 3737 E. Century Blvd., Lynwood, Calif. 90262; Richard M. Densmore, Fountain Valley, Calif.

[73] Assignee: Charles H. Klieman, Los Angeles, Calif.

[21] Appl. No.: 433,028

[22] Filed: Oct. 6, 1982

Related U.S. Application Data

[63] Continuation-in-part of Ser. No. 231,976, Feb. 6, 1981, abandoned, which is a continuation-in-part of Ser. No. 183,360, Sep. 2, 1980, Pat. No. 4,325,376, which is a continuation of Ser. No. 822,076, Aug. 5, 1977, abandoned.

[51] Int. Cl.³ .................. A61B 17/12; B31B 1/00
[52] U.S. Cl. .................. 128/325; 128/326; 227/19; 227/DIG. 1
[58] Field of Search .................. 128/325, 326, 334 R; 227/19, 119, DIG. 1

[56] References Cited

U.S. PATENT DOCUMENTS

| | | | |
|---|---|---|---|
| 4,425,915 | 1/1984 | Ivanov | 128/325 |
| 4,427,008 | 1/1984 | Transue | 128/325 |
| 4,430,997 | 2/1984 | DiGiovanni et al. | 128/325 |
| 4,450,840 | 5/1984 | Mericle et al. | 128/325 |
| 4,452,376 | 6/1984 | Klieman et al. | 128/325 |

FOREIGN PATENT DOCUMENTS 0086721 8/1983 European Pat. Off. .
2088723 6/1982 United Kingdom .

Primary Examiner—Gene Mancene
Assistant Examiner—C. W. Shedd
Attorney, Agent, or Firm—Spensley Horn Jubas & Lubitz

[57] ABSTRACT

A surgical clip applying device having a main body, a clip magazine coupled to the main body for holding a plurality of clips, clip deforming jaws coupled to the main body for receiving and deforming clips, a clip loading mechanism for loading clips from the magazine to a clip feed blade which moves clips from the clip magazine to the deforming jaws, and a spring activated actuating mechanism. The clip loading mechanism includes a double ratchet apparatus coupled to a pawl for advancing the clips through the magazine. The actuating mechanism includes handle portions, a ratchet member having a cam follower which is coupled to a camming surface which is in turn coupled to one of the handle portions, a spring connected to the main body and the ratchet member, and a latch adapted to engage the ratchet member. By movement of one of the handle portions with respect to the other handle portion, the camming surface engages the cam follower to store energy in the spring, which is retained therein via engagement of the latch with the ratchet member. In operation, a slight movement of one of the handle portions with respect to the other handle portion disengages the latch from the ratchet member so that the energy stored in the spring is converted into rapid forward movement of the clip feed blade. This forward movement causes the clip loading mechanism to advance a clip and, in addition, causes the clip feed blade to slide through the magazine to rapidly place a clip in the deforming jaws.

13 Claims, 15 Drawing Figures

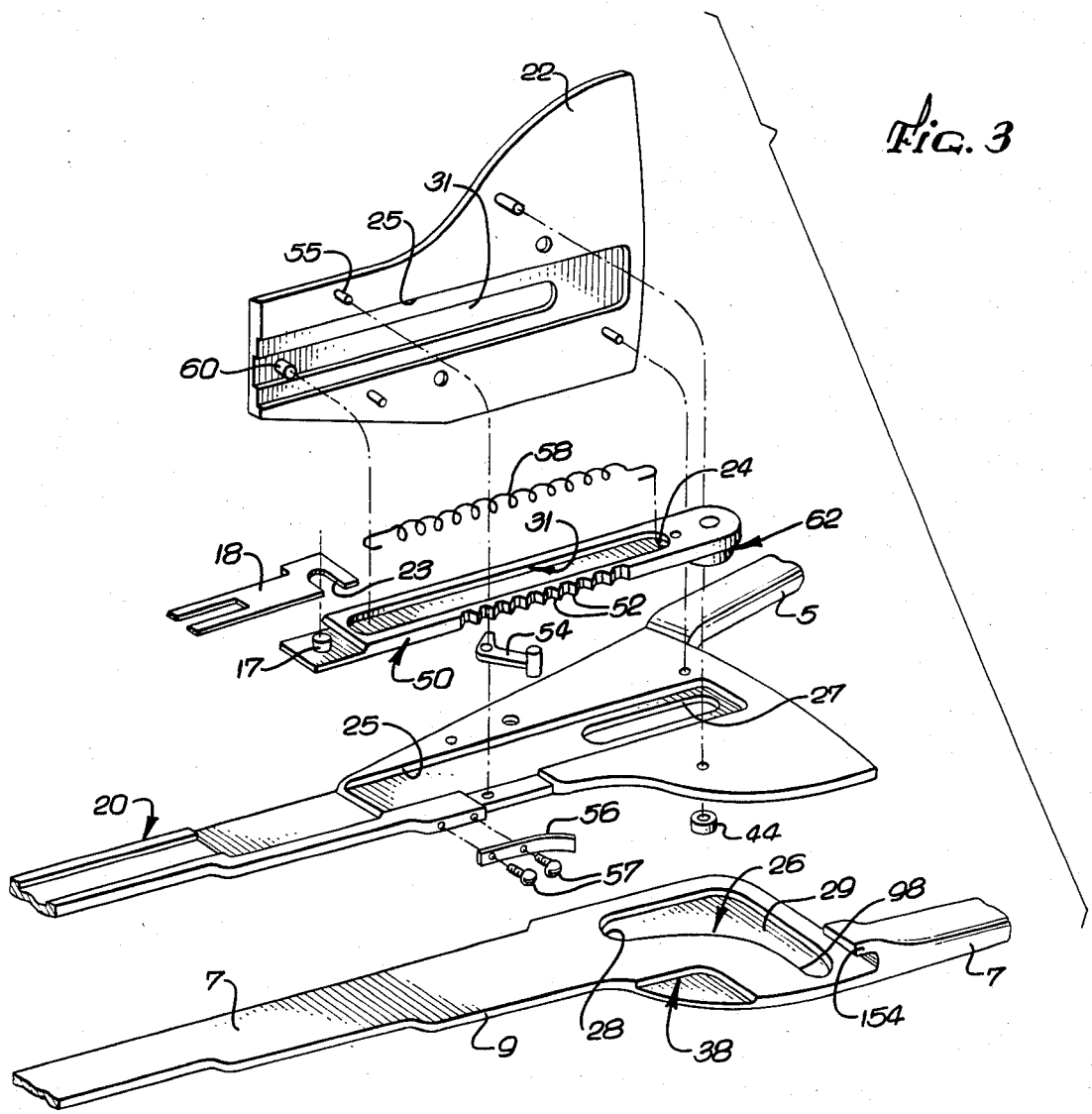
Fig. 3
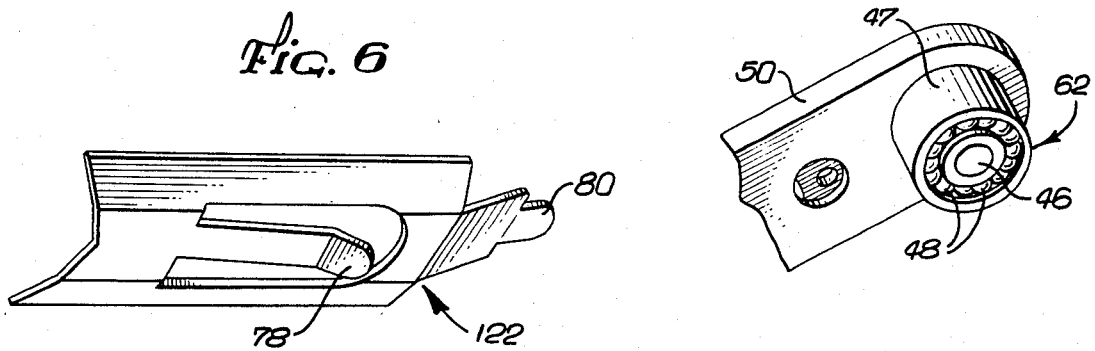
Fig. 6
Fig. 4

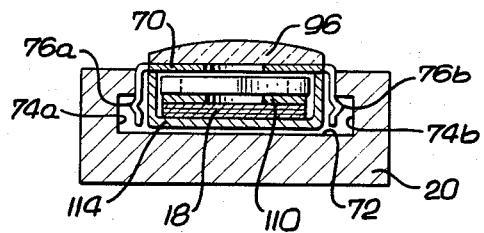
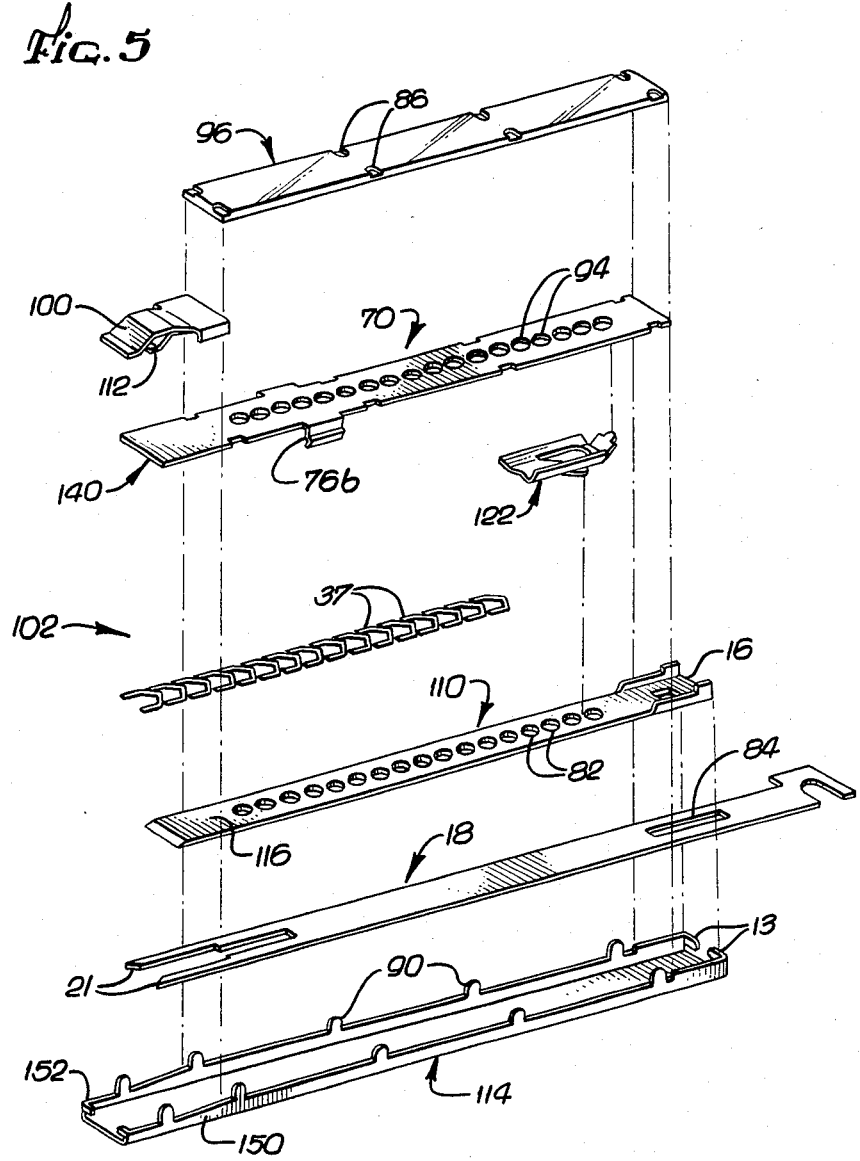

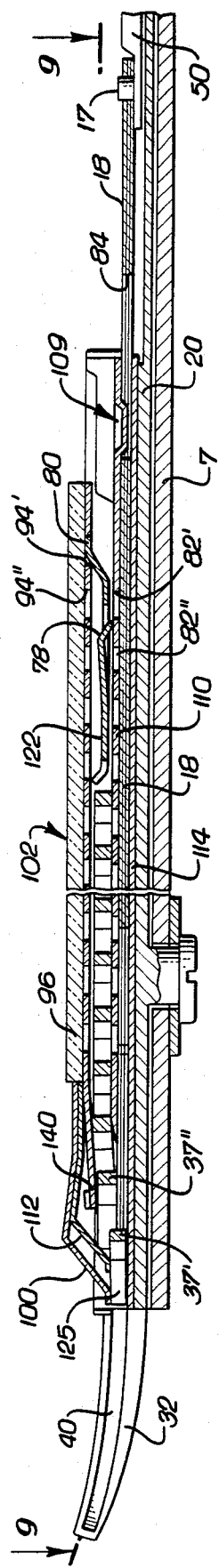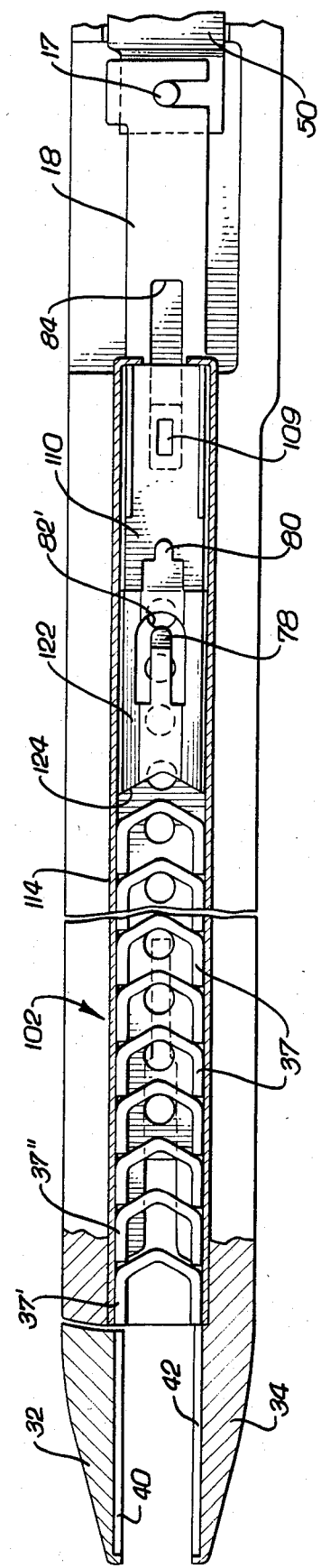

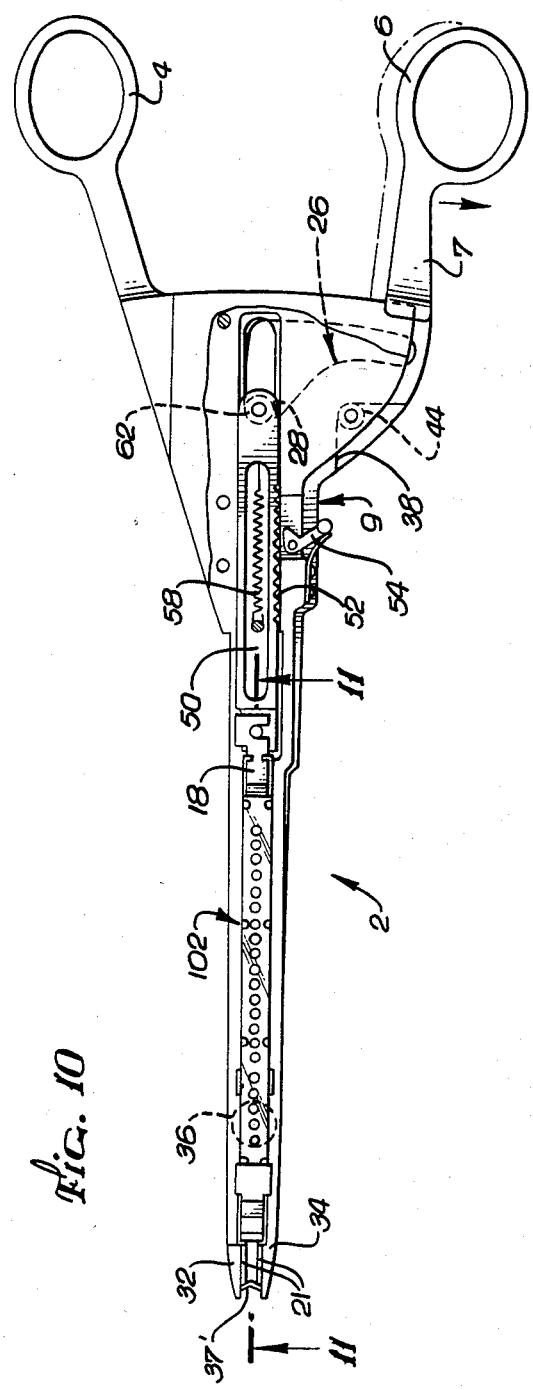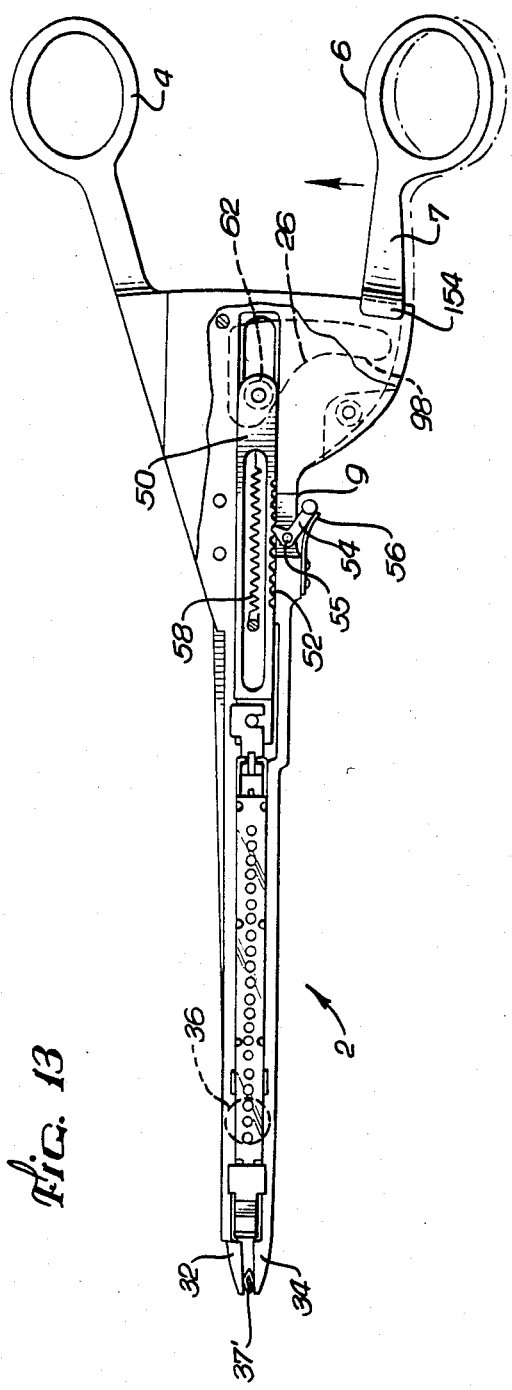

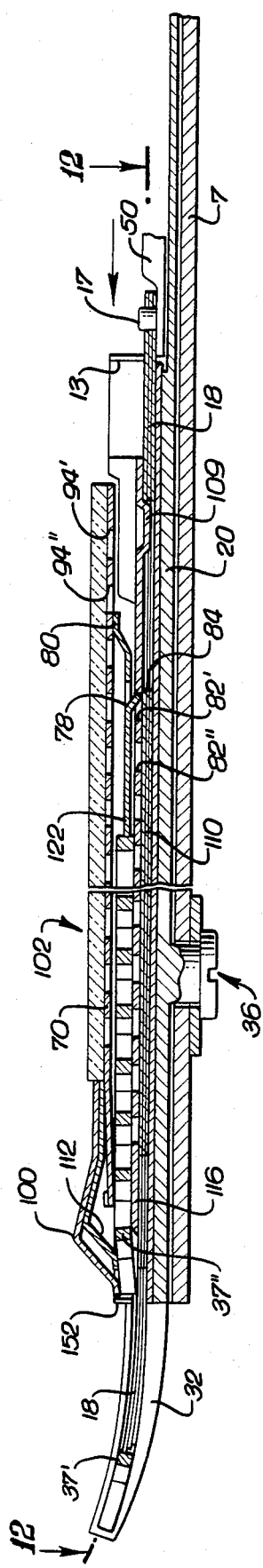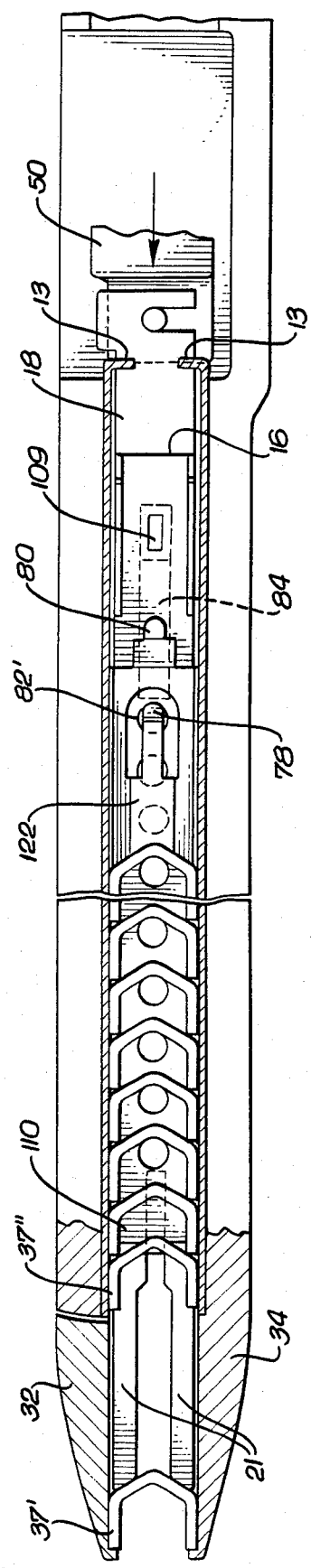

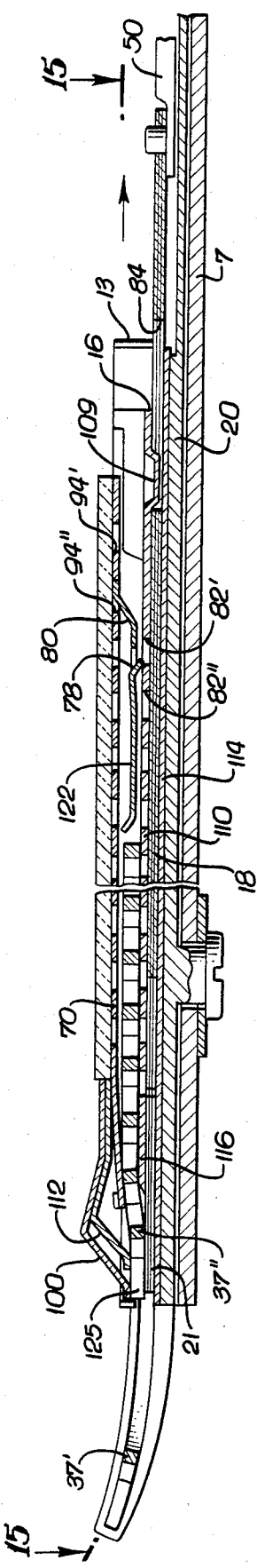
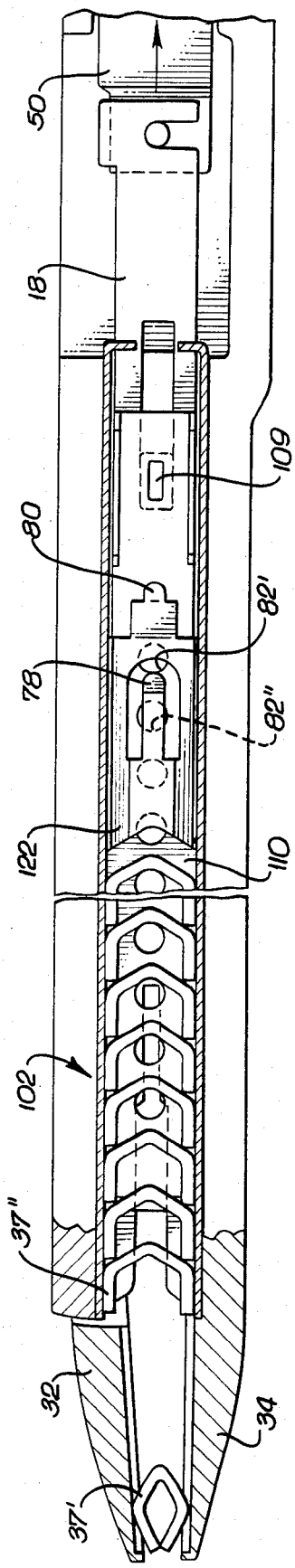

SPRING ACTIVATED HEMOSTATIC CLIP APPLICATOR

1. Copending Patent Applications

This application is a continuation-in-part of application Ser. No. 231,976 now abandoned entitled Spring Activated Hemostatic Clip Applicator, filed on Feb. 6, 1981, which is a continuation-in-part of application Ser. No. 183,360 now U.S. Pat. No. 4,325,376 entitled Hemostatic Clip Applicator, filed on Sept. 2, 1980, which is a continuation of application Ser. No. 822,076 filed on Aug. 5, 1977, and now abandoned.

BACKGROUND OF THE INVENTION

In U.S. Pat. No. 4,188,953 entitled Hemostatic Clip, issued on Feb. 19, 1980, and assigned to the present assignee, hemostatic clips adapted for utilization in the present invention and similar devices is disclosed.

In the above-referenced copending U.S. patent application entitled Hemostatic Clip Applicator, and assigned to the present assignee, a Hemostatic Clip Applicator for the strangulation of tubular members in a rapid and automatic manner is disclosed. That application is directed, in part, to a device having a main body, a clip cartridge, actuating handles, and clip deforming jaws. Disposed within the clip cartridge are a plurality of hemostatic clips, and a clip feed means which moves clips to the clip deforming jaws where the clips are deformed about a blood vessel or the like.

While the applicator noted in the preceding paragraph provides a novel method for automatically closing blood vessels and other fluid ducts, it requires the manual feeding of a hemostatic clip into the deforming jaws by the forward movement of one of two handles. That is, to operate that device, the surgeon must first move one of the handle portions to a forward position so as to load a hemostatic clip in the deforming jaws, and then return that handle portion to its neutral position. Once the surgeon has located the hemostatic clip around the tubular member to be closed, he squeezes both handle portions together resulting in the crimping of a clip about the blood vessel. When the surgeon is ready to close another blood vessel, this same sequence of moving one handle portion forward and then rearward must be repeated so as to sequentially load and close a clip.

In the other above referenced copending U.S. patent application entitled Spring Activated Hemostatic Clip Applicator, and assigned to the present assignee, an alternative hemostatic clip applicator is disclosed which also provides for the rapid and automatic strangulation of tubular members. That application is directed, in part, to a device in which energy is first stored and then released to automatically deliver a clip into the jaws of the instrument. In the illustrated embodiment of that application, with a slight upward movement of one of the finger loops, a clip is almost instantaneously delivered to the jaws of the instrument by the release of energy stored in a spring. Then, simply by moving the finger loops toward one another, the clip which has been loaded in the jaw portions can be deformed around a blood vessel or the like. Simultaneously with this crimping of the hemostatic clip, the instrument is again storing energy in the spring so that when another clip is needed, it can be readily available.

While this last noted clip applicator also provides a novel method for automatically closing blood vessels and other fluid ducts, it has been found that a noticeable additional force has often been necessary to "cock" the spring over and above that which is required to crimp the clip. This has resulted, in part, from the utilization of a spring which is capable of exerting a force sufficient to overcome frictional forces exerted by elements within the clip magazine. In particular, in the illustrated embodiment of this latter application, the clips in the magazine are pushed forward by a pawl which is engaged by a forward moving member which is coupled to the spring. The pawl also prevents the clips from moving backwards while the spring is being cocked. In that embodiment, the pawl is prevented from moving backward by the frictional engagement of two side arms disposed on either side of the pawl with the magazine housing walls. This frictional engagement of the pawl sidearms must be overcome by the spring in order to drive the pawl and consequently, the clips, forward. Since the force necessary to cock the spring increases the force necessary to close the finger loops and crimp the clip, it is desirable to minimize the requisite strength of the spring to minimize the cocking force of the spring.

It is toward the refinement of the devices disclosed in the copending U.S. patent applications noted above that the present invention is directed, and more specifically, toward a device which rapidly, yet almost effortlessly, loads and crimps a hemostatic clip in the deforming jaws of the instrument.

2. Field of the Invention

The invention relates to the field of devices useful in the application of hemostatic clips, and more specifically, to devices for the application of hemostatic clips used in the strangulation of blood vessels and other fluid ducts.

3. Prior Art

In a typical surgery procedure, a great many veins, arteries, and other blood vessels must be severed and closed. This is often a difficult and time consuming procedure since many vessels are located in obscure areas where there is little room in which to work. Thus, it is apparent that a device which would reduce the time required for closure of blood vessels would be a great benefit to both surgeon and patient.

One prior art attempt to provide a device which can more rapidly close a blood vessel is suggested by Jarvik, U.S. Pat. No. 4,146,466. The Jarvik device has a channel in the main body of the instrument which is integral with one of the jaws of the instrument. In the Jarvik device, a clip pusher moves the lower most clip in a clip stack through the channel in the main body to the jaws at the far end of the instrument. However, the pusher does not enter the jaws of the Jarvik instrument, but merely abuts the aft-most portion of the jaws without sliding therebetween. As a result, the jaws of the instrument are approximately the same length as the length of the clips, which can reduce visibility for the surgeon. In addition, upon application of the hemostatic clip by the Jarvik instrument, the pusher is positively prevented from returning from its farthest most position. Also, the Jarvik patent does not disclose an instrument which utilizes a spring loaded mechanism so as to move rapidly and accurately a clip from an internal clip magazine to the jaw portions of the instrument.

Accordingly, it is a general object of the present invention to provide an improved hemostatic clip applicator device for the strangulation of blood vessels and the like.

It is another object of the present invention to provide an improved automatic hemostatic clip applicator device which provides high visibility to the surgeon.

It is another object of the present invention to provide an improved hemostatic clip applicator device which rapidly and automatically feeds clips to its forward portion and then provides deformation of the clips about blood vessels.

It is yet another object of the present invention to minimize the friction in the operation of an automatic clip feeding hemostatic clip applicator.

It is still another object to provide an improved automatic clip feeding hemostatic clip applicator which simulates the feel of a manual hemostatic clip applicator.

It is another object to provide an improved cartridge which minimizes resistance to the advancement of each clip.

SUMMARY OF THE INVENTION

A hemostatic clip applicator device useful for rapidly and automatically applying clips for the strangulation of blood vessels and the like is provided. The device has a clip magazine coupled to the exterior of a main body, the clip magazine being adapted to hold a plurality of hemostatic clips. Attached to one end of the main body are clip deforming jaws adapted to hold and crimp a hemostatic clip about a blood vessel. Slideably disposed within the clip magazine is a clip feed means which is adapted to move clips from the magazine to the clip deforming jaws. The clip magazine has a clip loading means which sequentially loads the clip feed means with hemostatic clips from the magazine. Coupled to the clip feed means, the clip loading means and the clip deforming jaws is an actuating means. The actuating means includes handle portions coupled to the main body and an energizing means coupled to the main body, the clip feed means, the clip loading means and the handle portions. The energizing means is adapted to store energy and selectively supply that energy to the clip feed means and clip loading means.

By a slight outward movement of one of the handle portions, the energizing means is activated to supply the stored energy to the clip feed means so as to cause one of the clips stored in the clip magazine to be moved rapidly to the clip deforming jaws. The stored energy is also supplied to the clip loading means such that the next clip in the magazine is advanced for loading to the clip feed means. Once located in the clip deforming jaws, the clip can be crimped about a blood vessel or the like simply by moving the handle portions toward one another. As a consequence of this squeezing of the handle portions toward one another, energy is again stored in the energizing means so as to be available for a subsequent rapid placement of the next clip in the deforming jaws. This sequence of rapidly feeding clips to the clip deforming jaws and crimping them, may be repeated until the plurality of clips located in the clip magazine is depleted.

In comparison with the automatic clip applicator device disclosed in our co-pending U.S. application Ser. No. 281,976, the present invention reduces the force necessary to squeeze the handle portions together, by which the clips are crimped in the clip deforming jaws and the energy is stored in the energizing means. This is accomplished by reducing the friction exerted by the clip loading means, which must be overcome by the energizing means to effectuate the loading of a clip. As a result, the force required to be exerted by the energizing means and, consequently, the energy required to be stored by the energizing means, are correspondingly reduced. In the illustrated embodiment, the improved clip loading means includes a pair of ratchet bars in which one bar is moved in a reciprocating motion relative to the other by the energizing means. In addition, a pawl means is provided between the ratchet bars, which is adapted to alternately engage the ratchet bars in conjunction with the reciprocating motion of the ratchet bars to advance the clips held within the magazine.

In another aspect of the present invention, the force necessary to squeeze the handle portions together is also reduced by an improved energizing means. The energizing means includes a camming surface coupled to one of the handle portions and a low friction cam follower coupled to an energy storage means such as a spring. As the handle portions are squeezed together, the camming surface engages the cam follower which causes energy to be stored in the energy storage means in a particularly low friction manner.

The novel features which are believed to be characteristic of the invention, both as to its organization and its method of operation, together with further objects and advantages thereof, will be better understood from the following description in connection with accompanying drawings in which a presently preferred embodiment of the invention is illustrated by way of example. It is to be expressly understood, however, that the drawings are for the purposes of illustration and description only and are not intended as a definition of the limits of the invention.

BRIEF DESCRIPTION OF THE DRAWINGS

FIG. 3 is an exploded view of the energizing mechanism of the applicating device of FIG. 1;

FIG. 4 is a pictorial view of the cam follower portion of the ratchet connecting member of the applicating device of FIG. 1;

FIG. 5 is an exploded view of the clip magazine of the clip applicating device of FIG. 1;

FIG. 6 is an enlarged pictorial view of the pawl of the clip magazine of FIG. 5;

FIG. 7 is a cross-sectional view of the forward section of the clip applicating device taken along the lines 7—7 of FIG. 1;

FIG. 8 is a cross-sectional view of the forward section of the clip applicating device taken along the lines 8—8 of FIG. 1;

FIG. 9 is a side cross-sectional view of the clip applicating device taken along the lines 9—9 in FIG. 8;

FIG. 10 is a side view of the clip applicating device of FIG. 1 illustrating the device in its configuration immediately following the rapid loading of a clip into the jaws of the device;

FIG. 11 is an enlarged cross-sectional view of the forward portion of the clip applicating device taken along the lines 11—11 of FIG. 10;

FIG. 12 is a side cross-sectional view of the clip applicating device in its configuration as illustrated in FIG. 11;

FIG. 13 is a side view of the clip applicating device of FIG. 1 illustrating the simultaneous crimping of a hemostatic clip and the cocking of the energizing mechanism;

FIG. 14 is a cross-sectional view of the forward section of the clip applicating device of FIG. 1 illustrating the position of elements of the magazine at a time subsequent to that shown in the configuration of FIG. 13; and FIG. 15 is a side cross-sectional view of the clip applicating device taken along the lines 15—15 of FIG. 13.

DETAILED DESCRIPTION OF THE INVENTION

A spring activated hemostatic clip applicator device is disclosed which is useful in rapidly applying a sequence of hemostatic clips about blood vessels and other fluid ducts. The hemostatic clip applicator of the present invention may be used with hemostatic clips such as is described in our U.S. Pat. No. 4,188,953 issued on Feb. 19, 1980, entitled "Hemostatic Clip", or with any other suitably adapted hemostatic clip.

Figure 1:
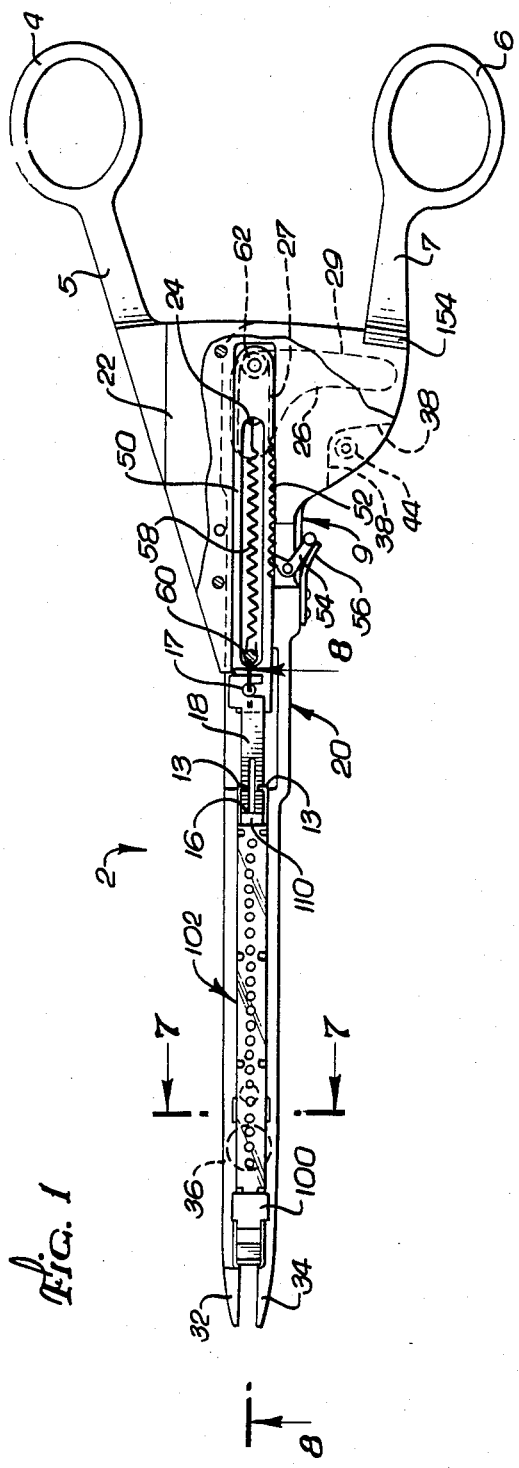
FIG. 1 is a side view of the clip applicating device of the present invention with a portion broken away.
Figure 2:
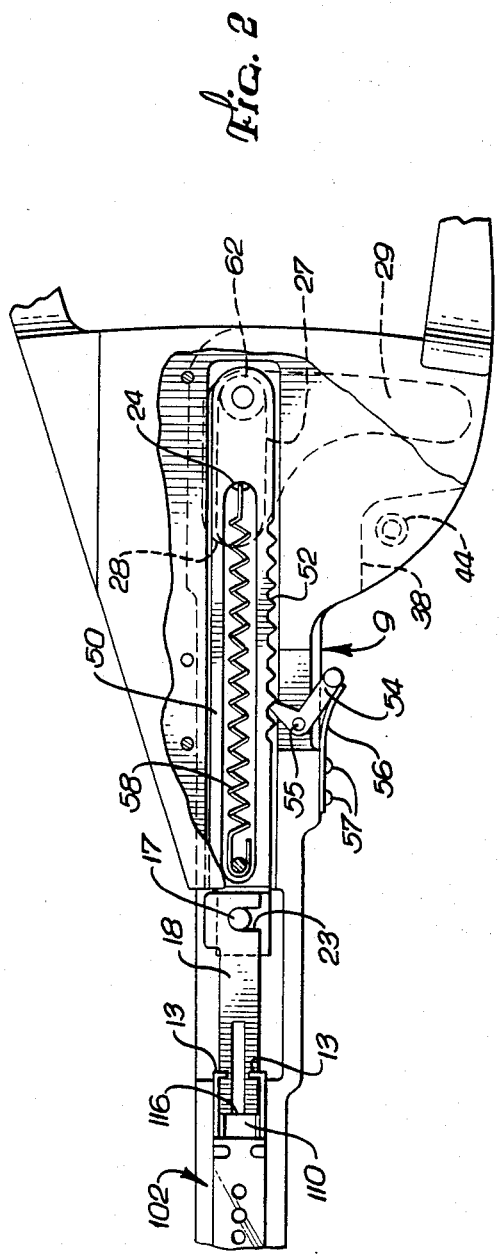
FIG. 2 is an enlarged view of the broken away portion of the applicating device of FIG. 1.

Referring to FIGS. 1, 2 and 3 the spring activated hemostatic clip applying device 2 of the present invention is shown with its actuating means in its "cocked" configuration. The actuating means is comprised of an energizing means, and handle portions. In the presently preferred embodiment, the energizing means is comprised of ratchet connecting rod or member 50, ratchet spring 58, and latch 54. The handle portions are comprised of an upper finger loop 4 and upper finger loop member 5, along with lower finger loop 6 and lower finger loop member 7. Upper finger loop 4 and upper finger loop member 5 are integral with main body 20.

As will be more fully described hereinbelow, clip feed blade 18 is a clip feed means which in the presently preferred embodiment is a blade member adapted to slide rapidly through clip magazine means 102 and into the forward portions (i.e., those portions to the left in FIG. 1) of device 2. Also, as will be described more fully hereinbelow, the rapid movement of clip feed blade 18 into the forward portions of device 2, and the corresponding movement of a hemostatic clip into the jaw members 32, 34 of device 2, is accomplished merely by activating the energizing means of the present invention.

Disposed within clip magazine means 102 are a plurality of hemostatic clips 37 (FIG. 9), and magazine 102 is adapted such that the individual clips are available to be moved forward by clip feed blade 18. Spring guide means 100 aids the movement of a clip from magazine 102 into the main body 20 of instrument 2.

Coupled to the forward portion of main body 20 is a clip deforming means adapted to deform a hemostatic clip 37 about a blood vessel or the like. In the presently preferred embodiment, the clip deforming means is comprised of upper jaw portion 32 and lower jaw portion 34. Upper jaw portion 32 is fixedly coupled to lower finger loop member 7 and pivotally coupled to main body 20 by upper jaw pivot 36, while lower jaw portion 34 is fixedly coupled to main body 20. When a hemostatic clip 37 has been fed from the clip magazine 102 into grooves 40 and 42 (FIG. 9) of jaw portions 32 and 34 by the interaction of clip feed blade 18 and the energizing means, the clip may be squeezed about a blood vessel by squeezing finger loops 6 and 4 together so that upper jaw portion 32 closes toward lower jaw portion 34.

Now referring more particularly to the energizing means of the present invention, reference is made to the main components of the energizing means—ratchet connecting member 50, latch 54, latch spring 56, and ratchet spring 58. As illustrated in FIGS. 1-3, ratchet member 50 is coupled to clip feed blade 18 by means of ratchet member pin 17 inserted into slot 23 of clip feed blade 18. The ratchet connecting member 50 is also coupled to lower finger loop 6 by cam follower 62 at the end of the ratchet connecting member. The ratchet connecting member 50 is slidably carried in a longitudinal groove 25 defined by cover plate 22 and main body 20 when assembled as indicated in FIG. 3. The main body 20 has a window 27 through which the cam follower 62 extends. The lower finger loop member 7 includes recess 29 which defines the camming surface 26. The cam follower 62 of ratchet connecting member 50 extends into this recess 29 from window 27 of main body 20. One end of ratchet spring 58 is coupled to main body 20 by pin 60 of cover plate 22, while the other end is coupled to ratchet connecting member 50 by slot 24. Ratchet spring 58 is carried in a groove 31 defined by cover plate 22 and ratchet connecting member 50 when assembled.

In the configuration illustrated in FIGS. 1 and 2, energy has been stored in the stretched ratchet spring 58, that energy being directed toward the forward movement of ratchet member 50 in groove 25 and the corresponding forward movement of clip feed blade 18. Energy remains stored in spring 58 because forward movement of ratchet member 50 is prevented by the engagement of latch 54 with the teeth or serrations 52 of ratchet 50. Latch 54 is held in engagement with ratchet member 50 by the urging of spring 56, that spring being coupled to main body 20 by rivets 57. In the presently preferred embodiment, ratchet spring 58 is a helical spring, although other types of springs could be readily utilized.

In operation, a slight movement of lower finger loop 6 away from upper finger loop 4 causes the lower edge 9 of lower finger loop member 7 to engage latch 54 and rotate latch 54 about pin 55 in a clockwise direction. This clockwise rotation of latch 54 causes latch 54 to disengage from the teeth 52 of ratchet member 50. With the removal of the impediment of latch 54, ratchet spring 58 is free to contract and drive ratchet member 50 forward. This forward movement of ratchet member 50 causes clip feed blade 18, coupled to ratchet member 50, to rapidly advance through the instrument and thereby immediately place a hemostatic clip 37 in the extreme ends of jaw portions 32, 34. As will be explained in more detail hereinbelow, the forward advance of clip feed blade 18 and the ratchet member 50 is controlled and fixed by the abutment of the cam follower 62 with the forward portion of cam surface 26 indicated at 28. Similarly, the rearward reach of clip feed blade 18 is controlled by the abutment of rearward stop 16 of lower ratchet bar 110, with end tab 13 of magazine 102.

It is important to note from FIG. 1 that the outward movement of upper jaw portion 32 is limited by the stop surface 38 of lower finger loop member 7 with stop pin 44 of main body 20. Thus, if a hemostatic clip is located in jaw portions 32 and 34, it may not accidentally be dropped by the over expansion of upper jaw 32 with respect to lower jaw 34.

Illustrated in FIG. 2 is the relationship of recess 29, cam follower 62, and the window 27 in main body 20. In the condition illustrated in FIGS. 1 and 2, lower finger loop 6 is free to travel inwardly and outwardly about pivot 36 within the confines of the travel of cam follower 62 within the recess 29 of lower finger loop member 7. This freedom of movement of lower finger loop 6, and the corresponding freedom of movement of upper jaw portion 32 with respect to lower jaw portion 34 has the following very useful advantage during a surgery. If a hemostatic clip 37 has been previously applied to a blood vessel or the like during surgery, and it becomes necessary to further crimp or secure that hemostatic clip 37, the freedom of movement of instrument 2, as illustrated in FIGS. 1 and 2, allows the surgeon to place the previously crimped hemostatic clip 37 between jaws 32 and 34 and make further crimping adjustment as necessary.

Finally, in reference to FIG. 2, it can be seen that cam follower 62 is free to move through window 27 in main body 2 when the latch 54 is released. Thus, when the energizing means induces a forward movement of ratchet member 50 and feed blade 18, cam follower 62 can freely travel from right to left in window 27.

FIG. 4 is an enlarged view of the cam follower 62 at the rearward end of the ratchet connecting member 50. As seen therein, cam follower 62 has an axle 46 on which is rotationally carried a roller wheel 47. Coupling wheel 47 to axle 46 is a plurality of roller bearings 48. As will be seen more clearly below, the cam follower 62 of the energizing means reduces the friction which occurs as the spring 58 is cocked, thereby easing the force required to squeeze the finger loops together.

FIG. 5 illustrates in greater detail the components comprising the clip magazine 102 and the clip feeding means of the present invention. Clip magazine 102 is comprised of a magazine housing 114, containing a plurality of hemostatic clips 37. Located within clip magazine housing 114 is lower ratchet bar 110 and clip feed blade 18 between housing 114 and lower ratchet bar 110.

Magazine housing 114 is affixed to main body 20 in a cavity 72 (FIG. 7) which has recesses 74a and 74b on either side. Magazine 102 further includes upper ratchet bar 70 which has a pair of dimpled tabs 76a and 76b which snap into main body recesses 74a and 74b, respectively. In this manner, upper ratchet bar 70 couples the magazine 102 to main body 20.

The clips 37 are aligned in a single forward facing row between ratchet bars 70 and 110. A pawl 122 is positioned behind the rearward most clip of magazine 102 and is provided to urge the clips forward. As will be more fully explained below, pawl 122 is actuated by the reciprocating forward and backward motion of lower ratchet bar 110 which is in turn moved by clip feed blade 18. As seen more clearly in FIG. 6, pawl 122 has a downwardly extending resilient tab 78 and an upwardly extending resilient tab 80. The tabs 78 and 80 alternately engage the recesses or holes 82 and 94 of ratchet bars 110 and 70, respectively, to advance the clips 37 forward, in conjunction with the reciprocating motion of the lower ratchet bar 110. The forward most clip is positioned by guide spring 100 and leaf spring 112 in front of clip feed blade 18. Completing magazine 102 of the illustrated embodiment is cover bar 96 which is affixed to housing 114 by housing tabs 90 bent over into corresponding recesses 86 of cover bar 96.

FIG. 8 is a cross-sectional view of the forward portion of clip applying device 2, as taken along lines 8—8 of FIG. 1. In the forward most portion of FIG. 8, it can be seen that there is a groove 40 disposed within upper jaw portion 32. Groove 40 in conjunction with the corresponding groove 42 (FIG. 9) in lower jaw portion 34 serves to guide and secure a hemostatic clip 37 as it is rapidly moved from the main body 20 of instrument 2 to the forward most portions of jaws 32, 34.

It can be seen from FIG. 8 that the forward movement of clip feed blade 18 through magazine 102 will move hemostatic clip 37' from its key position 125 through lower jaw portion groove 42 and ultimately to the extreme end of lower jaw portion 34. As illustrated in FIG. 8, jaw portions 32 and 34 can be curved away from main body 20 to allow better visibility during usage. Thus, feed blade 18 must be configured so as to be capable of being moved forward through grooves 40 and 42 while simultaneously bending away from main body 20 in grooves 40 and 42. In the presently preferred embodiment, this capability has been provided by constructing feed blade 18 of three layers of thin blades of metal in a laminated configuration. The three layers are only coupled at discreet points so that the feed blade 18 is able to move longitudinally through main body 20 while curving around grooves 40 and 42 in jaw portions 32 and 34.

It can also be seen in FIG. 8 that guide spring means 100 and leaf spring 112 are adapted to maintain clip 37' in its key position 125 until clip 37' is moved forward by feed blade 18. In addition, the end 140 of upper ratchet bar 70 is adapted to maintain clip 37'' in its proper position so that it is available to be moved into key position 125 so as to replace clip 37'. The end 140 of upper ratchet bar 70 is bent slightly downward following the taper of housing 114 indicated at 150 (FIG. 5).

It can also be seen in FIG. 8 that clip magazine 102 is comprised of a simply constructed housing 114 which is inexpensively stamped from stock material and then attached to the main body 20 by the upper ratchet bar tabs 76. Thus, clip magazine 102 is replaceably coupled to main body 20 so that when the clips 37 are depleted from magazine 102, that magazine 102 can be removed from instrument 2 and a new magazine 102 can be placed therein.

FIG. 8 also shows that lower ratchet bar 110 is coupled to clip feed blade 18 by means of extension member 109 which extends into slot 84 of feed blade 18. Because ratchet connecting member 50 is in its extreme retracted position, extension member 109 is abutting the extreme left end of slot 84. Also disposed within clip housing 114 is pawl 122 with its lower tab 78 disposed just ahead of a lower ratchet bar hole indicated as 82'. The upper pawl tab 80 is disposed in a hole 94' of the upper ratchet bar. Pawl 122 is positioned so as to abut the rearward most clip 37.

FIG. 9 is a side cross-sectional view of the forward portion of clip applying device 2 with ratchet connection member 50 again shown in its extreme retracted position. In this FIGURE, the clip feed blade lost motion slot 84 wherein is disposed extension member 109 of the lower ratchet bar, can be seen more clearly. Pawl 122 is shown in its extreme rearward position having tab 78 located just ahead of lower ratchet bar hole 82'. The leading edge 124 of pawl 122 is configured so as to conform to the bail portion of clips 37. As will be described more fully hereinbelow, pawl 122 is adapted to move clips 37 forward through magazine 102 when lower ratchet bar 110 is moved forward.

Now turning to FIG. 10, instrument 2 is illustrated in its configuration just following the spring activated loading of hemostatic clip 37' into jaw portions 32, 34. As noted in the discussion of FIG. 1, a slight downward movement of finger loop 6 with respect to finger loop 4 causes lower edge 9 of lower finger loop member 7 to abut and thereby rotate latch 54 in a clockwise direction so as to disengage latch 54 from teeth 52 of ratchet member 50. Immediately after this disengagement of latch 54 from ratchet member 50, the energy stored in ratchet spring 58 causes ratchet member 50 to snap forward, and thereby rapidly move clip feed blade 18 through magazine 102, and ultimately move hemostatic clip 37' into jaw portions 32, 34. This rapid forward movement of clip feed blade 18 is brought to an abrupt halt, by the abutment of cam follower 62 with stop surface 28 of camming surface 26 at just the point where clip 37' is properly positioned in jaws 32, 34.

It should be particularly noted in FIGS. 5 and 10 that the forward most end of clip feed blade 18 is split into two sections 21 which are arranged in a forked configuration. The abutment of forked ends 21 of clip feed blade 18 with the bail portion of hemostatic clip 37' provides the significant advantage of preventing rearward movement of clip 37' when the clip is being positioned around a blood vessel or the like. Furthermore, the forked configuration of the forward most end 21 of clip feed blade 18 has the significant advantage of not reducing visibility through jaw portions 32, 34.

FIG. 11 is a cross-sectional view of the forward most section of clip applying device 2, taken along the lines 11—11 of FIG. 10. Here also ratchet connecting member 50 has been moved to its full forward position as in FIG. 10. Because previous forward movement of ratchet member 50 and feed blade 18 have brought about abutment of low ratchet bar extension member 109 with the rear most end of lost motion slot 84, the further forward movement of clip feed blade 18 has resulted in forward movement of lower ratchet bar 110. This forward movement of lower ratchet bar 110 causes pawl lower tab 78 to drop in and engage hole 82', resulting in forward movement of pawl 122. Note, since upper ratchet bar 70 does not move but is fixed relative to housing 114, the resilient upper pawl tab 80 has been moved down out of the last upper ratchet bar hole 94' and has been moved past the next to last hole 94" by the forward movement of pawl 122. The forward movement of pawl 122 has, in turn, caused forward movement of clips 37 disposed within magazine 102. The initial movement of lower ratchet bar 110 before pawl 122 moves allows a tolerance in the dimensions of the magazine parts as well as the clips themselves.

In addition, the full forward movement of ratchet connecting member 50 has caused clip feed blade 18 to travel through much of upper jaw portion 32 and lower jaw portion 34 and thereby place clip 37' at the extreme end of jaw portions 32, 34. Thus, this full forward movement of ratchet member 50 has placed a clip in the loaded position in jaw portions 32 and 34 so that it is now ready to be placed about a blood vessel or the like.

It can also be seen in FIG. 11 that another hemostatic clip 37" has now been moved into the key position 125 so as to be available during the next spring activated loading sequence. It is important to note that clip 37" is resting on platform 116 of lower ratchet bar 110 and is held in place by guide spring 100 and leaf spring 112. Platform 116 prevents one or both legs of clip 37" from becoming disoriented within key position 125. Furthermore the downward taper of upper ratchet bar 70 guides the line of clips down to key position 125 and helps prevent the rearward clips from passing up and over the forward clips as the clips are driven forward. A safety stop 152 at the end of housing 114 prevents the clips from being ejected out of the housing by the forward motion of the lower ratchet bar 110 and pawl 122.

FIG. 12 is a cross-sectional side view of clip magazine 102 where, just as in FIG. 11, connecting member 50 has been brought to its full forward position. Cover plate 96 and upper ratchet bar 70 are not shown for clarity. Here, it can be seen that lower ratchet bar extension member 109, which is abutting the right most portion of lost motion slot 84, has now been moved forward by the forward movement of clip feed blade 18. The forward movement of ratchet extension member 109 has caused lower ratchet bar 110 to also move forward. Because lower tab 78 of pawl 122 is disposed in hole 82' of ratchet bar 110, the forward movement of ratchet bar 110 has resulted in the forward movement of pawl 122. Then, this forward movement of pawl 122 has caused the series of clips 37 contained in magazine 102 to also move forward. Furthermore, this continued forward movement of ratchet connecting member 50 has caused clip feed blade 18 to guide clip 37' through jaw portions 32 and 34 to the extreme portions thereof.

Now turning to FIG. 13, the configuration of spring activated clip applying device 2 while a hemostatic clip 37' is being crimped is illustrated. Due to the movement of lower finger loop 6 toward upper finger loop 4, and the resulting pivoting of upper jaw portion 32 around pivot 36, upper jaw portion 32 is moved toward lower jaw portion 34 so as to crimp hemostatic clip 37'.

There are two important occurrances to be noted as the result of this crimping operation illustrated in FIG. 13. First, it can be seen that forked ends 21 of feed blade 18 are simultaneously being retracted from jaw portions 32, 34 while being bent toward one another by the closing of jaw portions 32, 34. Second, as lower finger loop 6 is moved toward upper finger loop 4, energy is again being stored in ratchet spring 58 by the retraction of ratchet connecting member 50. This retracting movement of ratchet member 50 is caused by the movement induced by cam follower 62. As illustrated in FIG. 13, in phantom, cam follower 62 of ratchet connecting member 50 is coupled to lower finger loop member 7 via camming surface 26. Thus, as lower finger loop 6 is moved upward, camming surface 26 engages cam follower 62 so as to cause a retracting force to be applied to cam follower 62 and a corresponding retraction of ratchet member 50. That is, as finger loop 6 is lifted toward finger loop 4, the ratchet connecting member 50 is retracted. This retraction causes a stretching of spring 58 and results in a storage of energy therein.

It has been found that the freely spinning roller wheel 47 (FIG. 4) of the cam follower 62 together with the camming surface 26, provides an improved cocking mechanism for cocking spring 58. The resistance exerted by this mechanism to the closing of the finger loops is relatively small which contributes to the natural "feel" of the device. Furthermore, it is seen that the displacement of the ratchet connecting member, for each incremental movement of the finger loops together, can be selected by the particular shape of the camming surface 26 provided.

Although the cam follower 62 has been shown as a freely spinning wheel, it is recognized that other low friction cam follower devices may be used. For example, a fixed surface coated with teflon or other low friction plastics may be used to engage the camming surface 26.

As spring 58 is cocked, any forward movement of ratchet member 50 is prevented by the interaction of latch 54 with ratchet member 50. Because the lower edge 9 of lower finger loop member 7 is no longer interacting with latch 54, and because latch spring 56 is causing a counter-clockwise rotational movement of latch 54 about latch pivot 55, latch 54 is caught in one of the various ratchet teeth 52 disposed on the lower edge of ratchet member 50. As ratchet member 50 is retracted, latch 54 rides up and over each of the inclined teeth 52 of ratchet member 50 so as to continue to prevent forward movement of ratchet member 50. Of course, a variety of other mechanisms could be used in place of the ratchet member 50 and latch 54 so as to provide a releasable impediment to movement.

The lower finger loop member 7 has a tab 154 which overlaps the main body 20 and cover plate 22 to help prevent them from spreading from the lower finger loop member 7 as the finger loops are squeezed together to crimp the clips. A similar overhanging tab (not shown) is provided for the same purpose at the other end of lower finger loop member 7 adjacent jaw portions 32 and 34.

FIGS. 14 and 15 illustrate in greater detail the relationship of feed blade 18, lower ratchet bar 110 and upper ratchet bar 70 when the cocking and crimping motion of instrument 2 is more advanced than the configuration illustrated in FIG. 13. In comparison with FIG. 11, it can be seen in FIG. 14 that clip feed blade 18 has been moved in the rearward direction by the retracting motion of the ratchet connecting member 50. This rearward movement has caused the forked ends 21 of clip feed blade 18 to retract from jaw portions 32, 34, and the bending of forked ends 21 toward one another as jaw portions 32 and 34 converge.

Further, comparison of FIGS. 11 and 14 will disclose that lost motion extension member 109 has traveled the length of the lost motion slot 84 contained in feed blade 18. Because lost motion member 109 is a part of lower ratchet bar 110, this rearward movement of extension member 109 through lost motion slot 84 has resulted in little or no rearward movement of lower ratchet bar 110. Of course, the further rearward movement of feed blade 18 has caused a corresponding rearward movement of ratchet bar 110 due to the abutment of lost motion extension member 109 with the forward most section of lost motion slot 84. Ultimately, further rearward movement will be prevented when stop 16 on lower ratchet bar 110 abuts rear stop 13. The prevention of additional rearward movement of lower ratchet bar 110 also prevents further rearward movement of feed blade 18 due to the coupling thereof by extension member 109. The abutment of stop 16 with stop 13 is designed to coincide with the engagement of the cam follower 62 with the "flat" area 98 (FIG. 13) of camming surface 26. At area 98, the camming surface 26 is actually curved at a constant radial distance from the pivot point 36 such that the camming surface 26 at 98 no longer acts to retract the ratchet member 50 when the ratchet spring 58 is fully cocked.

An additional advantage of the "flat" area 98 is that it allows the finger loops 4 and 6 to be further closed to apply additional crimping pressure if necessary on the clip 37' in the jaws 32 and 34, without inducing a further retracting force on the ratchet member 50 after the ratchet spring 58 is fully cocked. This allows variable crimping forces to be applied as needed, yet the spring 58 is fully cocked each time the cam follower 62 reaches the area 98 of camming surface 26.

It can also be seen in FIG. 14 that retraction of ratchet member 50 and the corresponding retraction of feed blade 18 will allow clip 37'' in key position 125 to drop onto housing 114 when feed blade 18 has exited key position 125. This rearward movement of feed blade 18 does not result in rearward movement of the clip 37'' located in key position 125 because leaf spring 112 abuts the bail portion of clip 37'' and thereby retains clip 37'' in the key position 125.

In addition, rearward movement of clip feed blade 18 and lower ratchet bar 110 does not create rearward movement of the pawl 122 and the other clips 37. Pawl 122 is held stationary by upper tab 80 after tab 80 slides backward and into hole 94'' of upper ratchet bar 70, as shown in FIG. 14. As previously mentioned, the upper ratchet bar 70 does not move but is affixed to housing 114. Note that hole 94'' of upper ratchet bar 70 is adjacent hole 94' in which the upper tab 80 was previously disposed. Thus, when lower ratchet bar 110 moves rearward, pawl 122 is held stationary when pawl upper tab 80 engages upper ratchet bar hole 94'', while its lower tab portion 78 moves outward so that lower ratchet bar 110 slides under pawl 122. When clip feed blade 18 and lower ratchet bar 110 have returned to their rear-most position, lower tab portion 78 of pawl 122 will be past the next hole 82'' of lower ratchet blade 110. Note, the hole 82'' is adjacent the hole 82' where lower tab 78 previously was disposed. Thus the magazine is returned to the configuration shown in FIG. 8 except that the clip loaded in front of the clip feed blade 18 is now the next clip 37''. In addition, the pawl 122 has been advanced such that the upper tab 80 is disposed in the upper ratchet bar hole 94'' and the lower tab 78 is just ahead of the lower ratchet bar hole 82''. In this manner, sequential forward and rearward movement of ratchet bar 110 causes pawl 122 to progressively move forward, from one upper ratchet bar hole 94, to the next hole 94 and from one lower ratchet bar hole 82 to the next hole 82. In addition, the sequential forward and rearward ratchet bar 110 movement causes the upper pawl tab 80 to engage an upper bar hole 94 during rearward ratchet bar movement alternating with lower pawl tab 78 engagement with a lower ratchet bar hole during forward movement. Such progressive movement of pawl 122 causes, in turn, the progressive forward movement of clips 37.

Thus it is seen that as finger loop 6 is brought toward finger loop 4, upper jaw portion 32 is caused to abut lower jaw portion 34, and thereby completely crimp hemostatic clip 37'. This movement of lower finger loop 6 toward upper finger loop 4 has also caused the complete retraction of ratchet member 50 due to the engagement of cam follower 62 by camming surface 26. As a consequence of the counter-clockwise rotational force applied by latch spring 56, latch 54 continues to prevent the forward movement of ratchet 50. Thus, in this position, the energy has been restored in ratchet spring 58, so as to be available for subsequent instantaneous feeding of a hemostatic clip 37 into the jaws 32, 34.

Because the pawl 122 is held stationary against rearward movement only by the upper tab 80 engaging a hole of the upper ratchet bar 70, relatively little force is required to drive the pawl forward. The resiliency of upper tab 80 is such that little force is required to bend it down as the pawl moves forward and upper tab 80 is disengaged from the upper ratchet bar hole. As a result, a weaker ratchet spring 58 may be utilized and consequently, the force needed to cock the spring is correspondingly reduced. This factor also contributes to the natural feel provided by the instrument of the present invention.

It can be seen from the above description in conjunction with the associated illustrations, that the improved spring activated clip applying device 2 of the present invention provides an automatic and rapid feeding of hemostatic clips 37 into the jaws of the instrument 2. With only the slightest downward movement of finger loop 6, a clip is almost instanteously delivered to the jaw portions 32, 34. Then, simply by moving finger loops 4 and 6 toward one another, a hemostatic clip 37 which has been loaded in the jaw portions 32, 34 can be deformed around a blood vessel or the like. Simultaneously with this crimping of the hemostatic clip 37, the instrument is again storing energy in a spring so that when another clip is needed, it can be readily available. This process of inward and outward movement of finger loops 4 and 6 may be repeated rapidly, so that one vessel after another is closed by hemostatic clips 37, until the supply of clips in magazine 102 is depleted.

Even with this additional feature of almost instantaneous loading of hemostatic clips, the clip applying device 2 of the present invention provides the further advantages of high visibility to the user. Because the device 2 is of an extremely thin design, essentially the width of currently used hemostats, and because jaw portions 32 and 34 are curved away from the main body 20, and finally because the clip feed blade 18 is divided into thin forked sections 21 at its extreme end, a surgeon using clip applying device 2 will have a clear view of the vessel he is closing.

Furthermore, the clip applying device of the present invention closely simulates the feel which is provided by a conventional hemostat in which clips are manually inserted into the jaws of the hemostat. Devices which depart radically from the look and feel of conventional manual pliers-like hemostats have met significant resistance on the part of surgeons.

There has been described herein a new and novel clip applying device which has special utility for applying hemostatic clips to blood vessels and the like. However, it is to be understood that various alternate embodiments using the principles of the present invention may be readily incorporated. Thus, while specific embodiments of the present invention have been disclosed and described in detail herein, it will be understood by those skilled in the art that various changes in form and detail may be made therein without departing from the spirit and scope of the invention.

What is claimed is:

1. In a surgical clip applying device of the type having a main body, a clip magazine for holding a plurality of clips, clip deforming means for receiving and deforming the clips, clip feed means for moving the clips from the clip magazine to the deforming means, the improvement comprising, means for actuating the clip feed means including
(i) two handle portions; and
(ii) energizing means coupled to the main body, the clip feed means and one handle portion, for storing energy and selectively supplying the energy to the clip feed means, said energizing means including a camming surface coupled to said one handle portion, a cam follower, and a spring coupled to the main body, the cam follower and the clip feed means wherein movement of said one handle portion with respect to the other handle portion causes the camming surface to engage the cam follower and flex the spring thereby storing energy in the spring, and a subsequent movement of said one handle portion with respect to the other handle portion causes the energizing means to supply the energy stored in the spring to the clip feed means so as to cause a clip to be moved rapidly from the clip magazine to the clip deforming means and wherein the energizing means further includes a ratchet member coupled to the cam follower and a latch member pivotally coupled to the main body and adapted to engage the ratchet member so as to prevent release of the energy stored in the spring, and further adapted to disengage from the ratchet member when the energy is to be supplied to the clip feed means.

2. The clip applying device of claim 1 wherein the ratchet member includes a connecting rod coupling the spring to the clip feed means to supply the energy to the clip feed means when the latch member is disengaged.

3. The clip applying device of claim 2 wherein the main body defines a groove on one side of the main body in which said connecting rod is slidably carried and the main body further defines an aperture through which the cam follower coupled to the connecting rod extends to engage the camming surface of the energizing means.

4. The clip applying device of claim 3 wherein the connecting rod defines a groove to accommodate the spring and the device further comprises a cover plate coupling the spring to the main body and covering the connecting rod and the spring.

5. The clip applying device of claim 3 wherein said one handle portion has a recess which defines the camming surface.

6. In a surgical clip applying device of the type have a main body, a clip magazine for holding a plurality of clips, clip deforming means coupled to the main body for receiving and deforming the clips, clip feed means for moving the clips from the clip magazine to the deforming means, the improvement comprising means for actuating the clip feed means including:
(i) two handle portions coupled to the main body, at least one of the handle portions being pivotally coupled to the main body;
(ii) a connecting rod coupled to the clip feed means, said connecting rod having a cam follower and a serrated edge;
(iii) a spring coupled to the main body and to the connecting rod; and
(iv) a latch member coupled to the main body and adapted to engage the connecting rod serrated edge;
wherein pivotal movement of the pivotal handle portion with respect to the main body causes the camming surface to engage the cam follower which causes a retraction of the connecting rod and a corresponding distortion of the spring from its quiescent configuration, and return of the connecting rod is prevented by engagement of the latch member with the connecting rod serrated edge until a pivotal movement of the pivotal handle portion away from the other handle portion disengages the latch member from the serrated edge thereby allowing the spring to return to its quiescent configuration with a corresponding rapid sliding of the connecting rod thereby actuating the clip feed means.

7. In a surgical clip applying device of the type having a main body, a clip magazine for holding a plurality of clips, clip deforming means coupled to the main body for receiving and deforming the clips, clip feed means for moving the clips from the clip magazine to the deforming means, the improvement comprising, energizing means coupled to the main body and the clip feed means, for storing energy and selectively supplying the energy to the clip feed means to actuate the clip feed means, said energizing means including a camming surface, a cam follower and energy storage means for storing energy when the cam follower is actuated;

latch means for latching the cam follower to retain the energy stored in the storage means; and linkage means for moving the camming surface to engage the cam follower thereby actuating the cam follower, and for releasing the latch means to cause the energizing means to supply the energy stored in the storage means to the clip feed means so as to cause a clip to be moved rapidly from the clip magazine to the clip deforming means.

8. The clip applying device of claim 7 wherein the cam follower includes a roller wheel rotatably carried on the cam follower, for engaging the camming surface.

9. The clip applying device of claim 8 wherein the cam follower includes a plurality of roller bearings on which the roller wheel is rotatably carried to reduce the rotational friction of the roller wheel.

10. A surgical clip applying device comprising:
a main body;
a housing wherein a plurality of clips are stored;
clip deforming means coupled to the main body for receiving and deforming the clips
clip feed means for moving a clip from the housing to the deforming means,
clip loading means for sequentially loading clips to the clip feed means, said clip loading means including a first ratchet bar coupled to the housing, a second ratchet bar coupled to the clip feed means and adapted to be moved in a reciprocating forward and rearward motion, and pawl means for urging the clips through the housing, said pawl means having means for alternately engaging the second ratchet bar as the second ratchet bar moves forward such that the pawl means is moved forward with the second ratchet bar, and for engaging the first ratchet bar as the second ratchet bar moves rearward to prevent rearward movement of the pawl means;
two handle portions coupled to the main body; and
energizing means coupled to the main body, the clip feed means, the clip loading means and one handle portion, for storing energy and selectively supplying the energy to the clip feed means and the clip loading means, said energizing means including a camming surface coupled to said one handle portion, a cam follower, and a spring coupled to the main body, the cam follower, the clip feed means and the clip loading means wherein movement of said one handle portion with respect to the other handle portion causes the camming surface to engage the cam follower which flexes the spring thereby storing energy in the spring and which also moves the second ratchet bar rearward; and a subsequent movement of said one handle portion with respect to the other handle portion causes the energizing means to supply the energy stored in the spring to the clip feed means and the clip loading means so as to cause a clip to be moved rapidly from the clip magazine to the clip deforming means and to cause the second ratchet bar and pawl means to move forward to load a clip to the clip feed means.

11. In a surgical clip applying device of the type having a main body, a clip magazine for holding a plurality of clips, clip deforming means coupled to the main body for receiving and deforming the clips, clip feed means for moving the clips from the clip magazine to the deforming means, the improvement comprising, linkage means for actuating the clip feed means including:

two handle portions coupled to the main body wherein one handle portion has a recess which defines a camming surface;

a cam follower; and a spring coupled to the main body, the cam follower and the clip feed means, wherein movement of said one handle portion with respect to the other handle portion causes the camming surface to engage the cam follower and flex the spring thereby storing energy in the spring, and a subsequent movement of said one handle portion with respect to the other handle portion causes the energy stored in the spring to be supplied to the clip feed means so as to cause a clip to be moved from the clip magazine to the clip deforming means.

12. The clip applying device of claim 11 further comprising a ratchet member coupled to the cam follower and a latch member pivotally coupled to the main body and adapted to engage the ratchet member so as to prevent release of the energy stored in the spring and further adapted to disengage from the ratchet member when the energy is to be supplied to the clip feed means.

13. The clip applying device of claim 12 wherein the main body defines an aperture through which the cam follower extends to engage the camming surface of the one handle portion.

* * * * *